United States Patent

Cheng et al.

[11] Patent Number: 5,848,974
[45] Date of Patent: Dec. 15, 1998

[54] LUNG PROTECTION ELECTROCAUTERY

[76] Inventors: Wang Cheng, 1619 84 St., Brooklyn, N.Y. 11214; Xiang Wang, 164 Eric La., Lansdale, Pa. 19446

[21] Appl. No.: 593,391
[22] Filed: Jan. 29, 1996
[51] Int. Cl.$^6$ ....................................................... A61B 5/08
[52] U.S. Cl. ............................................ 600/532; 600/537
[58] Field of Search ..................................... 128/716, 721, 128/720, 725

[56] References Cited

U.S. PATENT DOCUMENTS 5,553,615  9/1996  Carim et al. ............................ 128/633

Primary Examiner—Angela D. Sykes
Assistant Examiner—Stephen D. Huang

[57] ABSTRACT

The present invention reliably provides a lung protection function for an electrocautery device by unitizing an automatic bovie activation/inactivation unit. The lung protection unit utilizes a threshold calculated from the maximum and minimum airway pressure signal in a ventilator or an anesthesia machine to inactivate the bovie before the maximal lung expansion reaches the bovie during a thoracic surgery. Bovie is activated again as soon as the lung expansion level decreases to below the threshold level. This device is an attached optional unit or can be built into a standard electrocautery equipment.

20 Claims, 6 Drawing Sheets

I: INPIRATION  E: EXPIRATION  VT: TIDAL VOLUME  V̇: PRESENT FLOW
PAW: AIRWAY PRESSURE

VT: TIDAL VOLUME  V̇: PRESENT FLOW  PAW: AIRWAY PRESSURE

LUNG PROTECTION ELECTROCAUTERY

FIELD OF THE INVENTION

This invention relates in general to an electrocautery system with an automatic activation/inactivation unit controlled by the expansion of the lungs, and in particular, to an electrocautery system controlled by electrical signals converted from an airway pressure in ventilator and/or anesthesia devices during endotracheal intubation for a thoracic surgery.

BACKGROUND OF THE INVENTION

An electrocautery system is a routine equipment for a thoracic surgical procedure. Its basic function is cutting and coagulation, some more advanced models may have the function of suctioning. The actual cutting unit is generally referred to as the "bovie", for the historical reason that one of the earlier and most popular electrocautery devices was named "Bovie". During a general thoracic surgery, surgeons sometimes have difficulty in using electrocautery due to the interference from the expansion of the lungs. Maximal expansion of the lungs may obstruct a bleeding point which needs a coagulation. Occasionally and unexpectedly, bovie can cut or burn the lung tissue and can cause an air leak and bleeding. In order to avoid an iatrogenic lung injury by bovie, surgeons usually use large gauze pad or hand to isolate the lungs from coagulation points. However, for some situation it is difficult or impossible to isolate the lungs. For instance, when cutting an incision into the chest wall, the lungs underneath the pleura could not be isolated simply because they usually can not been seen. Therefore, the pleura through intercostal incision usually is punctured with a scalpel handle, rather than bovie or blade. The remainder of the intercostal incision is opened with scissors and while the surgeon's index finger of the opposite hand is inserted to protect the lung. Using scissors to cut intercostal tissue or parietal pleura can cause bleeding. Bovie can not be used for this situation because the lung is not reachable for gauze pad protection. Another example is that in peripheral adhesions of the lungs or the chest wall tumor, a large area of separation between the lung and parietal pleura has to be acquired with the help of a gauze pledget and scalpel, or a large area of parietal pleura needs to be cut off. Often times during these situation, there will be a lot of bleeding points which imply best application of bovie for coagulation. However, due to lung's expansion and deflation back and forth, surgeon often prefers to use a blade to avoid an iatrogenic injury by bovie, therefore bovie's use is limited. Other similar situation may be cited where the advantage of bovie can not be fully appreciated.

The consequence of a lung injury by bovie is bleeding or air leak. It becomes a complication of thoracic surgery if the surgeon does not recognize it during the surgery. Patient will suffer from drainage of blood and air from a chest tube in a extended time period, or in some extreme cases, reopening the chest to suture the leak.

This invention describes an apparatus which can overcome the above mentioned disadvantages. It has an optional lung protection function. It can attach or be built into a standard electrocautery device. In this apparatus, a pressure detecting unit mounted in a ventilator or an anesthesia machine converts the machine controlled airway pressure into an electrical signal. A predetermined threshold calculated from the maximum and minimum values of this signal detects the onset of the maximal expansion of the lungs. This threshold is then used to dynamically activate/inactivate the electrocautery. Therefore, in a surgical field, when a lung expansion is about to reach the bleeding point where bovie is being used, bovie will be turned off automatically until passing the lung expansion to avoid burning the lungs. No similar invention in patent document has been found.

SUMMARY OF THE INVENTION

The present invention has the primary object of providing a method and apparatus to inactivate the electrocautery device before a maximal lung expansion reaches the bovie in use, therefore avoiding iatrogenic lung injury, or any living tissue injury.

The present invention has the further object of enhancing bovie to a wider application field.

The present invention has the further object of shortening surgical time, for example, using bovie to cut and coagulate intercostal tissue full layer, therefore benefiting the patient recovery as a result.

An electrocautery system, in general, has a suitable generator which provides a high frequency (usually 0.5 MHz or higher), high voltage (usually 4000 volts or higher) current that is transmitted to a small surgical electrode having a thin knife-like type to be applied to a patient. The relatively extremely small area of contact by the electrode with the patient provides an intense current in a highly localized area, producing a cutting action, or coagulation, depends on the type of waveform generated by the generator. In general, for cutting purposes, the generator is activated to produce a continuous sine wave signal. For coagulation, the generator may be selectively activated to produce a pulsing signal. The time duration for the bovie temperature to rise or drop between operating mode and standby mode is at the level of microseconds. The heat is only generated during the actual operation. Any heat generated or heat residue on bovie during standby is negligible. The extremely fast rise and drop response time make this present invention valid and practical. Therefore the key factors that warrantee the validity of the present invention are the bovie's extremely fast temperature drop-and-rise time and its negligible residue heat during standby mode because the assumptions for this invention to be valid are that the temperature drop time is so short that the immediate residue heat on bovie after inactivation is totally negligible and it does not cause any tissue cutting or burning in a medical sense. In fact, it has been tested and proven in clinical practices, that the operating surgeon can literally use bovie to touch the lung tissue, or any part of living tissue intentionally or unintentionally, immediately after bovie is turned off from either low or high temperature position, the residue heat on bovie does not cause any cutting or burning in any degree. It is based upon this fact that this present invention holds its practical application.

In brief, the method of the present invention includes converting a machine controlled airway pressure of either a ventilator or an anesthesia device into an electrical signal by a pressure transducer. This signal represents the airway pressure change which is strictly machine controlled, or indirectly represents the expansion of the lungs, from inhalation to exhalation. The lungs expand and compress during inhalation and exhalation, respectively. The converted electrical signal is then used to calculate a dynamic threshold which controls the activation/inactivation switch of the bovie.

The reader skilled in the art will recognize other objects and advantages of the invention, from a reading of the following brief description of the invention, the detailed description of the invention, and the appended claims.

BRIEF DESCRIPTION OF THE DRAWINGS

In the drawings, like numerals are employed to indicate like elements throughout.

The foregoing summary as well as the following detailed description of the preferred embodiments of the invention will be better understood when read in conjunction with appended drawings. For the purpose of illustrating the invention, there is shown on the drawings embodiments which are presently preferred. It should be understood, however, that the invention is not limited to the precise arrangements and instrumentality shown.

DETAILED DESCRIPTION OF THE PREFERRED EMBODIMENTS

Figure 1:
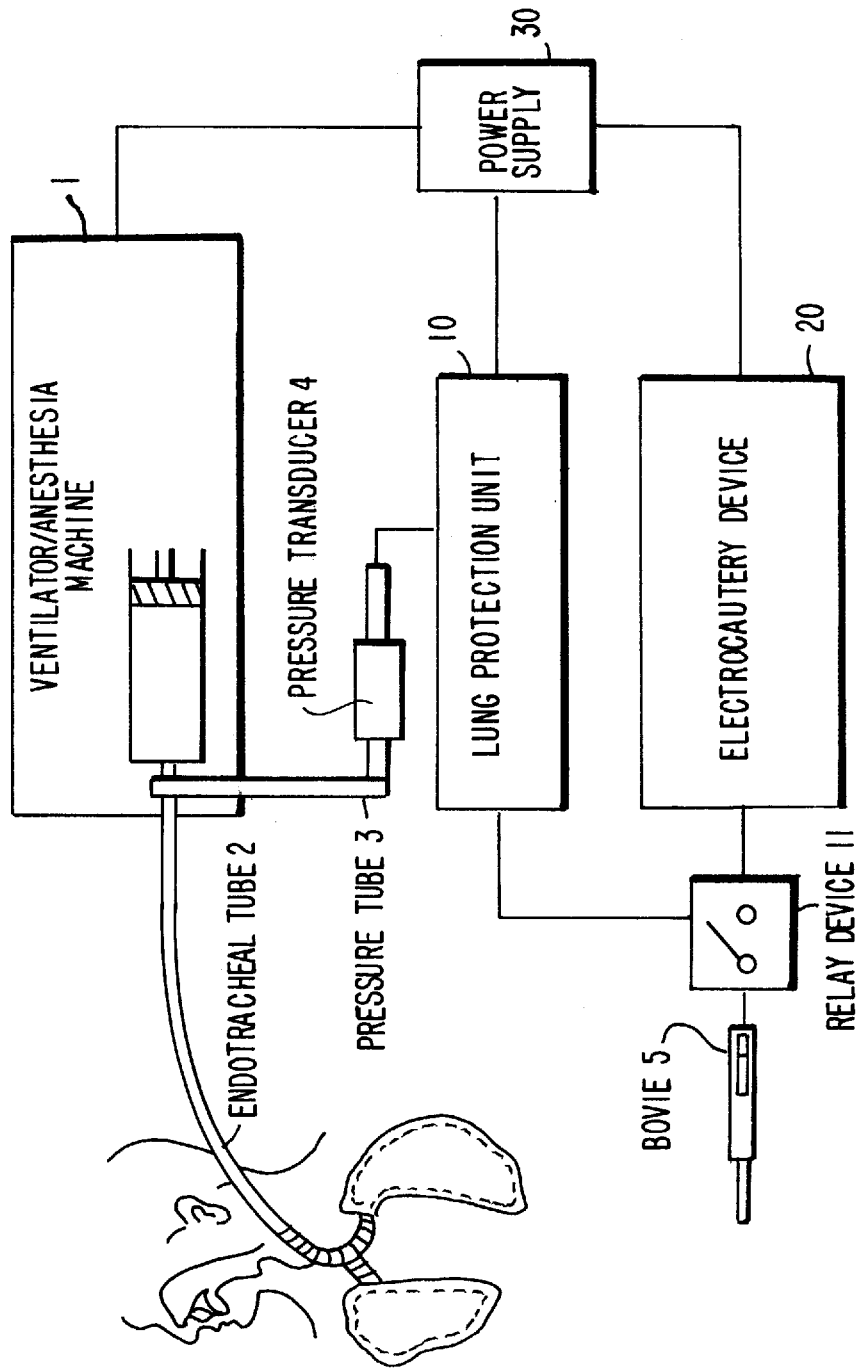
FIG. 1 depicts the schematic diagram of the present invention, showing the relationship among airway pressure in a ventilator and/or an anesthesia machine, an electrocautery device and the lung protection unit.
Figure 2:
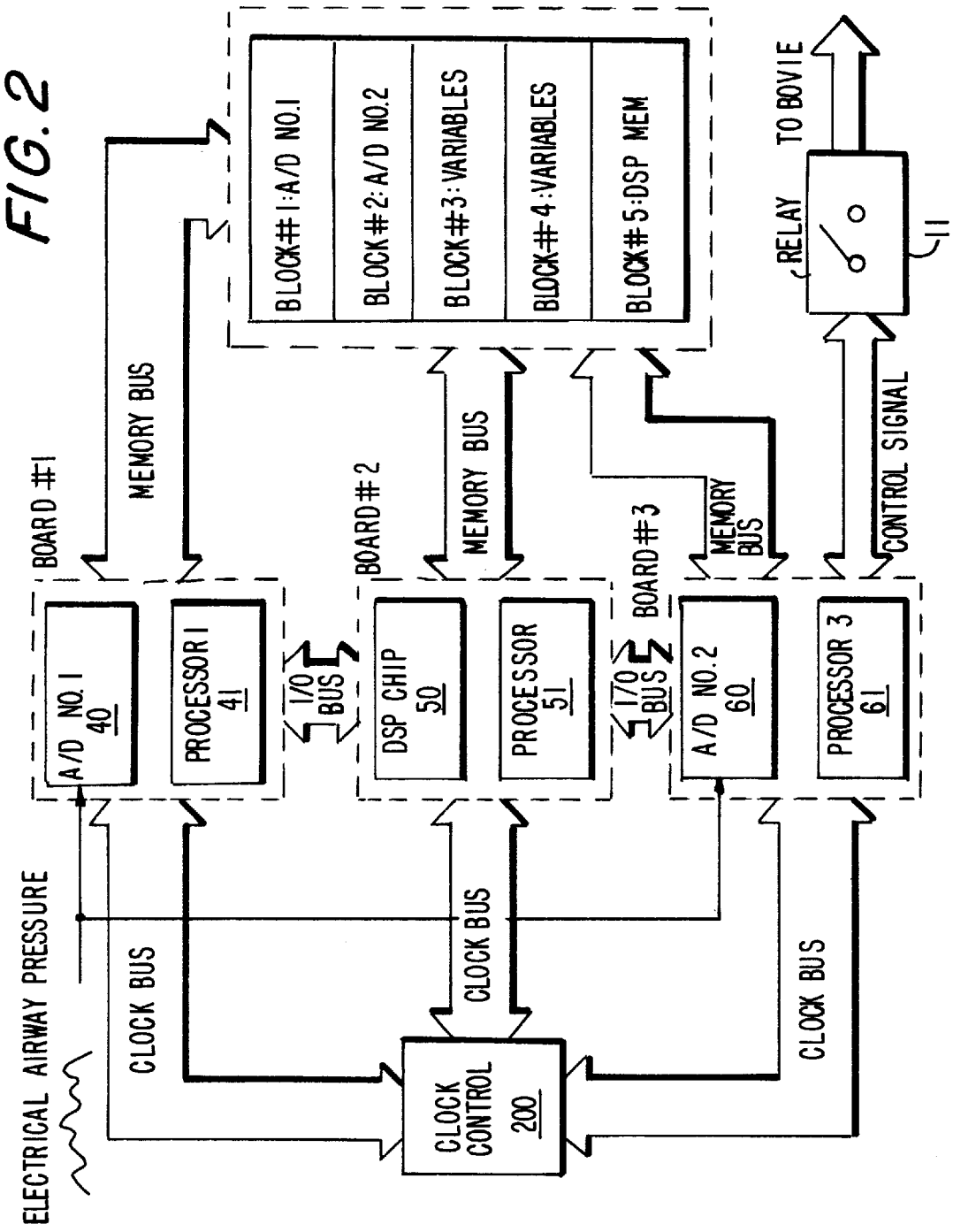
FIG. 2 is the system design schematic diagram.
Figure 3A:
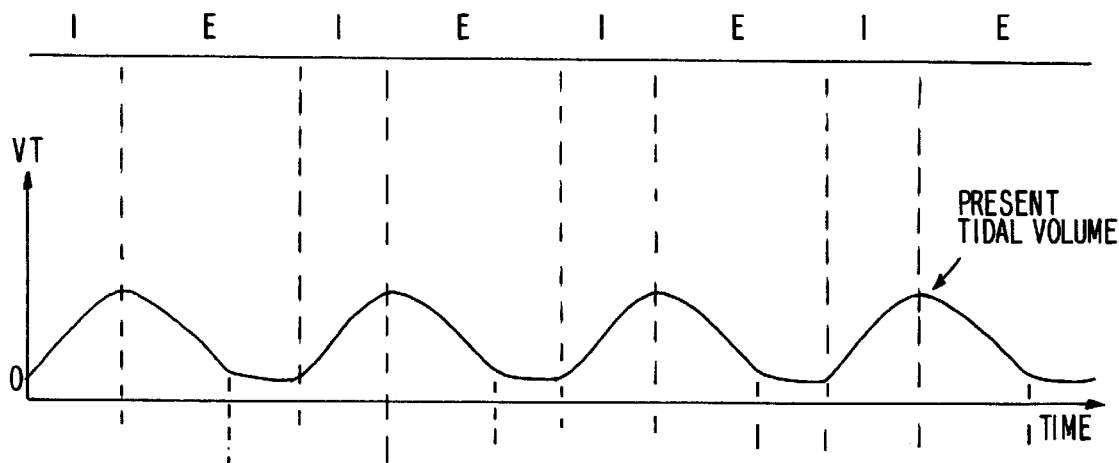
FIG. 3(a) demonstrates several typical airway pressure waveforms during controlled mechanical ventilation (CMV).
Figure 3B:
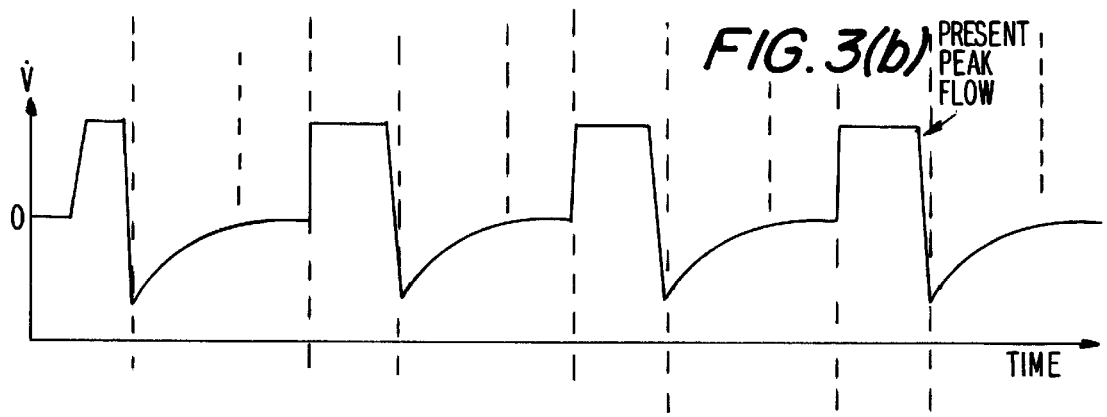
FIG. 3(b) demonstrates several typical airway pressure waveforms during pressure controlled ventilation (PCV).
Figure 3C:
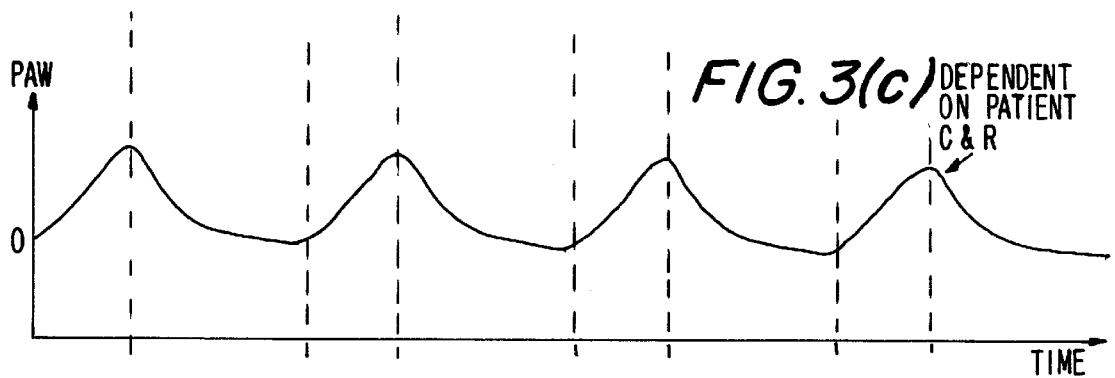
Figure 3D:
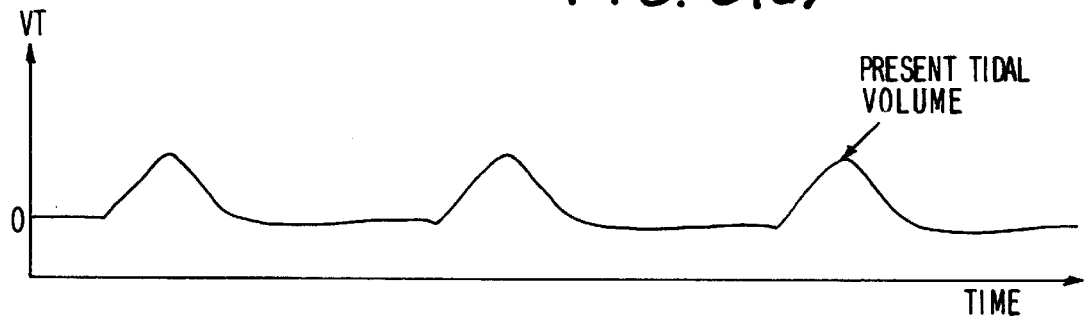
Figure 3E:
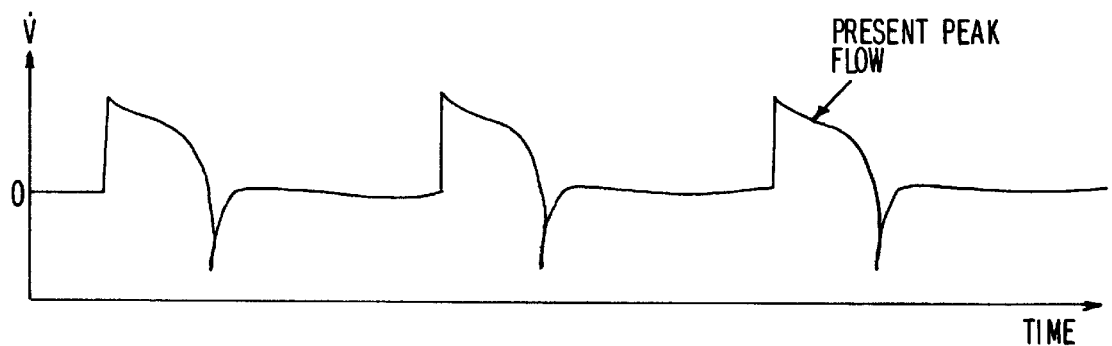
Figure 3F:
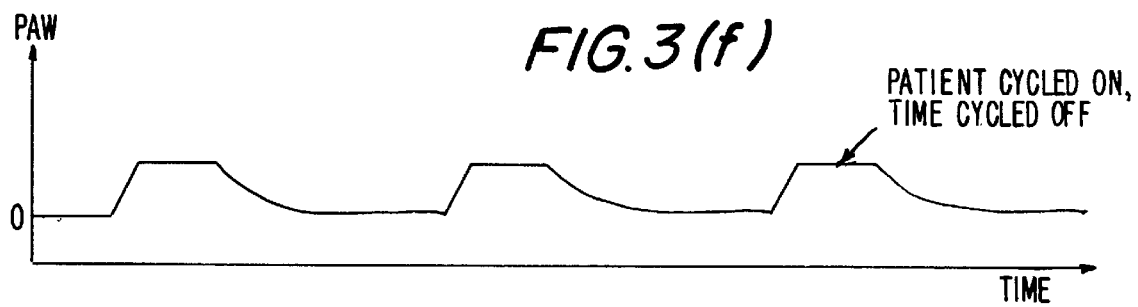
Figure 4:
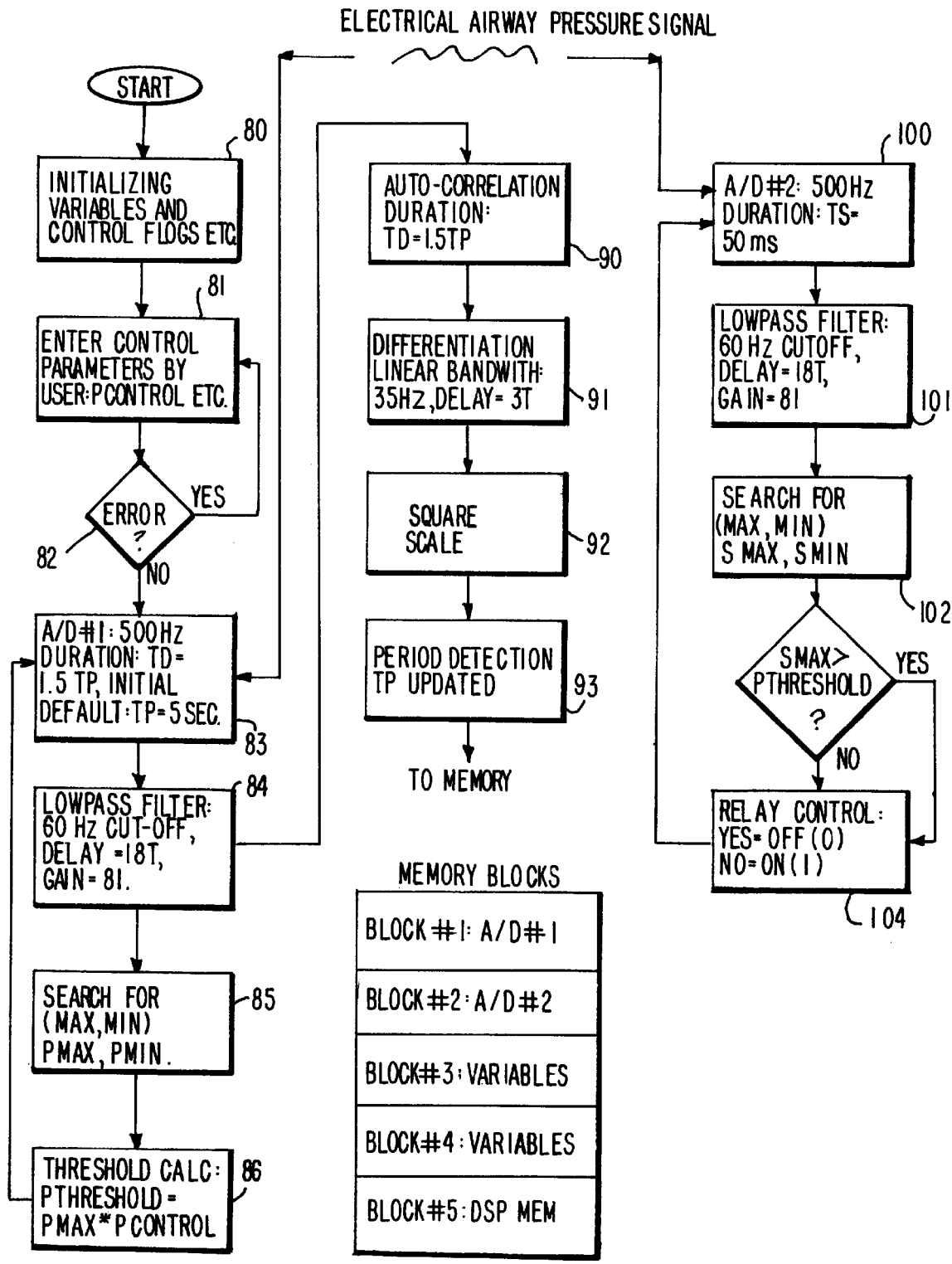
FIG. 4 is the software flow chart of the lung protection unit.
Figure 5A:
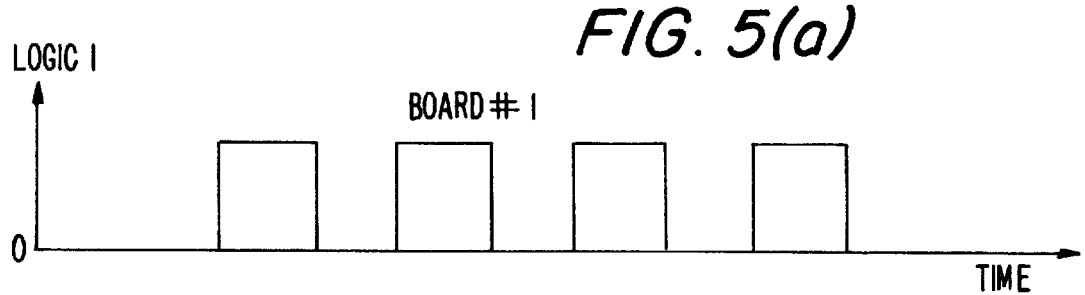
FIG. 5 is the lung protection unit system clock.
Figure 5B:
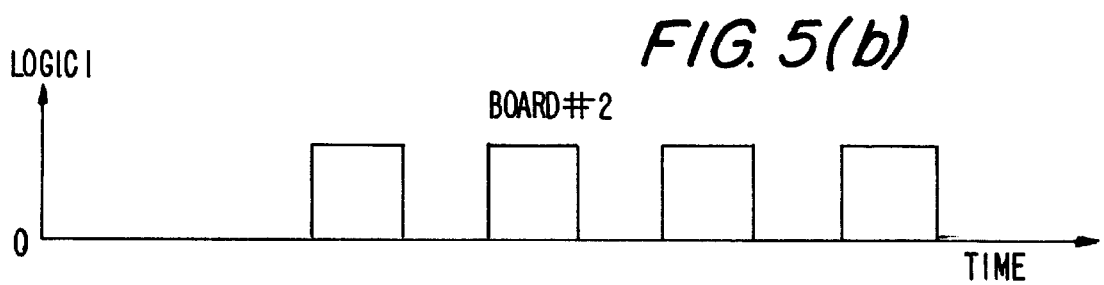
Figure 5C:
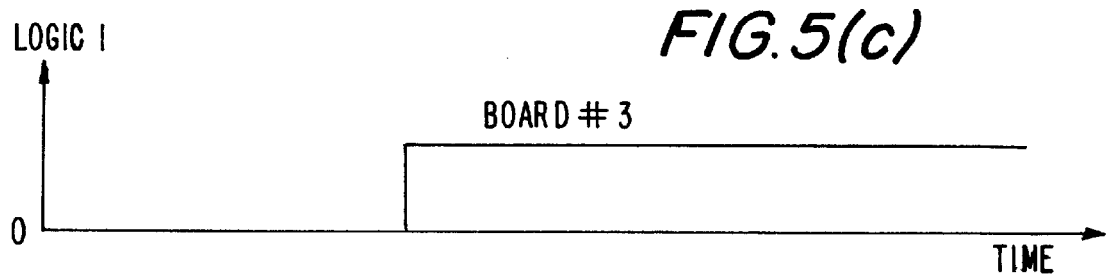

Mechanical ventilator support involves the delivery of flow and pressure to the patient's airway in order to effect changes in lung volume. The volume of air that is inhaled during inspiration with quiet breathing and leaves the lungs passively during expiration is the tidal volume ($V_T$). The time durations for a total inspiration and expiration are called the inspiration and expiration time ($T_I$ and $T_E$), respectively. The ratio of these two is called the I:E ratio.

The pattern of flow, pressure and volume delivery to a patient is termed the "mode" of ventilation support. Each mode, then, has its own characteristic flow, pressure, and volume graphics. In general several major modes are available:

(1) Controlled Mechanical Ventilation (CMV)—In this mode, the tidal volume $V_T$ and flow rate for each breath are clinician-set (volume cycled). The mechanical breath rate is also preset and all breaths are time cycled. As a result, $V_T$, $T_I$, $T_E$ and I:E ratio are all fixed. No spontaneous breath is allowed.

(2) Assist CMV (ACMV)—In the Assist CMV mode, as in the CMV mode, the tidal volume and flow rate for each mechanical breath are clinician-set (volume cycled). A minimum mechanical breath rate is also set as backup mandatory rate. Unlike the CMV mode, where all breaths are time cycled, Assist CMV permits patient cycling, therefore, spontaneous breathing is possible during this mode.

(3) Pressure Controlled Ventilation (PCV)—PCV is a mode of ventilator support in which the clinician controls the inspiratory time and the inspiratory pressure. Delivered flows are whatever is necessary to attain the desired inspiratory pressure, and volume is dependent upon the interaction of these settings and the respiratory system compliance and resistance.

(4) Synchronized Intermittent Mandatory Ventilation (SIMV)—SIMV is a mode in which there are both mechanical breaths and spontaneous breaths. The number of mechanical breaths is also preset by the clinician. The mechanical breaths may be either patient cycled or time cycled if the patient is apneic or bradypneic. The number of spontaneous breaths is determined by the patient and may vary from minute to minute.

(5) Intermittent Mandatory Ventilation (IMV)—This mode is similar to SIMV except that the mechanical breaths are delivered at regular intervals without regard to the patient's activity.

(6) Continuous Positive Airway Pressure (CPAP)—CPAP is a spontaneous breathing mode in which a constant positive airway pressure is usually maintained throughout the spontaneous breathing cycle.

In clinical environment, clinicians may utilize one or combination of the above mentioned modes to assist the patient. However, during thoracic surgery, no spontaneous breathing is allowed. The electrocautery device can not be utilized for surgical cutting until spontaneous breathing is completely eliminated. Instead, only machine controlled ventilation is allowed. Therefore, in general, only the controlled mechanical ventilation (CMV) and pressure controlled ventilation (PCV)—without patient assist—are used during surgical intervention.

Pressure is generally measured in the ventilator circuitry. It may also be measured in the inspiratory limb or expiratory limb internal to the ventilator. Although separated from the airways by the endotracheal tube, the pressure is still referred to as airway pressure. Due to this reason, spontaneous breath has negative pressure during inspiration, and positive pressure during expiration. On the contrary, mechanical breath has positive pressure during inspiration and negative pressure during expiration.

Maximal lung expansion is related directly to the maximum volume delivery, not necessarily to maximum pressure when a pressure plateau is present in the airway pressure waveform. However, maximum volume is reached at the end of the maximum pressure plateau, therefore, relating to maximum lung expansion. Since volume and flow waveforms are not attainable in general, therefore, airway pressure waveforms are the most commonly used signal for clinical analysis.

As mentioned earlier, no spontaneous breathing is allowed during surgical intervention, therefore, airway pressure has a fixed $T_I$, $T_E$ and I:E ratio strictly preset by the clinician. However, since lung compliance can change during the course of surgery, therefore the airway pressure can vary from beat to beat in order to accommodate the desired volume. As a result, the airway pressure waveform morphology may change from beat to beat, although usually not rapid. Thus, the airway pressure waveform can be considered only as a pseudo-periodic signal.

In the controlled ventilation mode, breath rate can vary as wide as from 3 to 120 beat per minute (BPM). Therefore the airway pressure waveform can have a frequency range of at least from 0.05 Hz to 2 Hz or wider.

The present invention utilizes the positive relationship between airway pressure and lung expansion, which is the core principle of the lung protection unit 10, to control a relay device 11 that will activate/inactivate the bovie 5 of the electrocautery system 20 during thoracic surgery. The airway pressure can be obtained by a pressure transducer 4 placed inside the endotracheal tubing system 2 or it may also be measured in the inspiratory limb or expiratory limb internal to the ventilator 1. The main task therefore, is to dynamically identify the maximum airway pressure or end of the maximum airway pressure plateau if any, for each cycle in real time. Since the airway pressure can vary according to lung compliance from beat to beat as mentioned earlier, therefore, accurately and rapidly identifying the maximum airway pressure within each cycle is one of the major contributions of this invention.

The present invention will preferably give user the choice of selecting a range of control levels: $P_{control}$, in a continuous or discrete mode, for example: off, 10% and 25% etc. In order to achieve the best real-time effect that guarantees a prompt control of the bovie 5 in the actual operating environment, the system design may utilize three hardware sections, they may be in the form of one compact board or three separate boards to minimize any possible delay in time. The first one is the Detection Board, which utilizes A/D converter 40 and micro-processor 41 to sample and search for the maximum airway pressure and calculate the control threshold; the second one is the Digital Signal Processing (DSP) Board, which utilizes a DSP chip 50 and microprocessor 51 to perform the high resolution and large scale signal processing; the third one being the Activation Board, which utilizes A/D convertor 60 and microprocessor 61 to use the user selected threshold to activate/inactivate the bovie by checking the actual airway signal in a real-time mode. The three boards are synchronized by a system clock 200.

On board #1, an iteratively and dynamically set time duration $T_D$ of the analog airway pressure signal is first converted into a digital signal by an A/D converter 40 with sample rate of 500 Hz. This dynamically computed time interval $T_D$ is one and half of $T_P$, namely, $T_D=1.5*T_P$ where $T_P$ is the airway pressure signal period/cycle that is calculated iteratively and dynamically by board #2. At the initial boot up, a default period $T_P$ is used until it is updated by board #2. Therefore, the maximum delay when the system is turned on would be the default time duration $T_D$. According to the Nyquist Theorem, to avoid aliasing phenomenon, sample rate must be at least twice the highest signal frequency component. At a sample rate of 500 Hz, aliasing is avoided because all the signal components are greatly and significantly lower than 500 Hz. The A/D converter 40 is set to be differential to reduce the common mode error; preferably, it has a resolution of 12 bit or higher with binary format. The A/D converter 40 may be, for example, a Data Translation Model DT2811/PGH.

The digitized signal is preferably passed into an allocated memory board, for example, a RAM chip 70, and stored in binary format for subsequent processing where digital filters are employed for further signal processing.

All digital filters are preferably designed to employ only integer coefficients. This allows the filters to operate in near real-time on a relatively simple microprocessor such as the IBM or Motorola microprocessors 41, 51 and 61, which are also employed to perform the remaining processing steps. The all-integer filter designs are both simple to program and fast to execute. They have proven to be more than capable of handling at relatively high speed the signal filtering required by the present invention. The filters use only a relatively small amount of multiplier and additional components, all with integer coefficients.

The digitized electrical airway signal is first low-pass filtered in 84 at 60 Hz to eliminate any possible high frequency interference. The usual auto-regressive moving average (ARMA) system can be represented by the equation:

$$y[n]=a_1y[n-1]+\ldots+a_my[n-m]+b_0x[n]+\ldots+b_kx[n-k]$$

For a low-pass filter, consider a special case of the moving average (MA) system:

$$y[n]=x[n]-x[n-k]$$

Its transfer function is:

$$H(z)=1-z^{-k}$$

where $z=e_{sT}$ and T is the sample interval. The k zeros in the z-plane are the roots of $1-z^{-k}=0$.

Consider the case k=12 for the z-plane represented by a real abscissa (X axis) and an imaginary ordinate (Y axis), i.e., Z(x,y)=Z(real,imaginary). If a zero at z=(1,0) of the unit circle for the real and imaginary values in the z-plane, respectively, is cancelled, then the following low-pass filter transfer function is obtained:

$$H(z)=(1-z^{-k})/(1-z^{-1})$$

This transfer function yields the recursive relation:

$$y[n]=y[n-1]+x[n]-x[n-k]$$

To improve the side lobes(−14 dB), second or third order zeros and poles may be employed:

$$H(z)=(1-z^{-k})^2/(1-z^{-1})^2,$$

or $$H(z)=(1-z^{-k})^3/(1-z^{-1})^3$$

which greatly improves the sidelobes (−27 dB, −42 dB). The recursive equation becomes:

$$y[n]=2y[n-1]-y[n-2]+x[n]-2x[n-k]+x[n-2k]$$

or $$y[n]=3y[n-1]-3y[n-2]+y[n-3]+x[n]-3x[n-k]+3x[n-2k]-x[n-3k]$$

The total order of this system has become 2k (or 3k). For k=12, the total system needs to preserve only 24 (or 36) data points.

A preferred low-pass auto-regressive moving average filter 84 for this invention is employed having a nominal bandwidth=±55.5 Hz, sidelobes=−27 dB, k=9, T=0.002 Sec (for sample rate of 500 Hz), Delay=18T, Gain=81, having the following transfer function and recursive formula:

$$H(z)=(1-z^{-9})^2/(1-z^{-1})^2$$

$$y[n]=2y[n-1]-y[n-2]+x[n]-2x[n-9]+x[n-18]$$

The low-pass filtered signal is then stored into the memory board 70, block #1, for further processing.

The low-pass filtered signal is then further searched in 85 for a maximum value $P_{max}$. In order to dynamically update the threshold: $P_{threshold}$ in 86, $P_{max}$ is then multiplied by a user selected control level $P_{control}$, namely, $$P_{threshold}=P_{max}*P_{control}$$

$P_{threshold}$ is then stored into memory board 70, block #4, for global variable use.

In theory, only statistical ensemble averaging can be used to define the mean, correlation, covairance, and power spectral density descriptors of random processes. However, in practice one does not typically have an ensemble of waveforms from which to evaluate these statistical descriptors: It is thus desirable to estimate all these statistical properties from a single sample waveform x[n] by substituting time averages for ensemble averages. The property required to accomplish this is ergodicity. A random process is said to be ergodic if, with probability 1, all its statistics can be predicted from a single waveform of the process ensemble via time averaging. The concept of ergodicity required the assumption that the data be stationary up to fourth moments. For a process to be stationary, the statistics must be independent of the time origin selected. While theoretically we might want to store the entire waveform of infinite duration, it is generally impractical. Generally we would like to avoid such a large delay in processing. It is thus practical and appropriate to assume that the airway pressure waveform satisfy all the conditions mentioned above. Therefore, the methodology of utilizing the auto-correlation technique to identify the period and thus the maximum and minimum values of the airway pressure is preferred in this invention.

Correlation, cross-correlation or auto-correlation, is the close mathematical cousin of convolution. It is in some ways similar, however, because the two functions that go into a correlation are not as conceptually distinct as were the data and response functions which entered into convolution. Rather, in correlation, the functions are represented by different, but generally similar, data sets. Correlation is investigated by comparing them both directly superposed, and with one of them shifted left or right. In cross-correlation, the two data sets are two random processes; in auto-correlation, the two data sets are the same random process.

A correlation can be denoted by Corr(g,h)[n] and is a function of lag n. The correlation will be large at some value of n if the first function g is a close copy of the second h but lags it in time by n, i.e., if the first function is shifted to the right of the second. Likewise, the correlation will be large for some negative value of n if the first function leads the second, i.e., is shifted to the left of the second. The relation that holds when the two functions are interchanged is:

$$Corr(g,h)[n]=Corr(h,g)[-n]$$

The correlation of two sampled functions g[k] and h[k], each periodic with period N, is defined by:

$$Corr(g, h)[j] = \sum_{k=0}^{N-1} g[j + k]h[k]$$

The discrete correlation theorem says that this discrete correlation of two real functions g[n] and h[n] is one member of the discrete Fourier transform pair:

$$Corr(g,h)[j]=G[k]H[k]^*$$

where G[k] and H[k] are the discrete Fourier transforms of g[j] and h[j], and asterisk * denotes complex conjugate. Obviously, for auto-correlation, we have:

$$Corr(g,g)[j]=G[k]G[k]^*$$

and this is always symmetric with respect to positive and negative lags.

Thus we can compute the auto-correlation of the the electrical airway pressure waveform by using the FFT as follows: FFT a data set that contains at least one breath cycle, put results into two temporary buffers, multiply one resulting transform by the complex conjugate of the other, and inverse transform the product. The result $r_k$ will formally be a complex vector of length N. However, it will turn out to have all its imaginary parts zero since the original data set is real. The components of $r_k$ are the values of the correlation at different lags, with positive and negative lags stored in the by wrap-around order: The auto-correlation at zero lag is in $r_0$, the first component; the auto-correlation at lag 1 is in $r_1$, the second component; the auto-correlation at lag −1 is in $r_{N-1}$, the last component; etc.

Just as in the case of convolution we have to consider the end effects, since our data will not, in general, be periodic as intended by correlation theorem. We can use zero padding. In general practice, if a correlation for lags as large as ±K is expected, then we must append a buffer zone of K zeros at the end of both input data sets.

Corr(g,g) computes the auto-correlation of signal set data[1, . . . ,n] with length n including any zero padding. n must be an integer power of two. The answer is returned as the first n points in array [1, . . . ,2*n] with length 2*n stored in wraparound order, i.e., auto-correlations at increasingly positive lags are in array [1] (zero lag) on up to array[n/2]. This large amount of computation is preferably done by a digital signal processing chip 50 on board #2 to gain speed and accuracy. The auto-correlation data are stored onto RAM chip, block #5 for subsequent processing.

The auto-correlation array[1, . . . ,2*n] is then differentiated by a digital differentiator 91 to extract high frequency component.

Consider an ideal, continuous time differentiator and its respective frequency response:

$$y(t)=d[x(t)]/dt \text{ and } H(j\Omega)=j\Omega$$

Since the input signal is restricted to be bandlimited, it would be satisfactory if the continuous response could be:

$$Heff(j\Omega) = j\Omega, |\Omega| < \pi/T_i$$
$$= 0, |\Omega| > \pi/T$$

The corresponding discrete-time differentiator has the following frequency response and is periodic with period 2p:

$$H(e^{j\omega})=j\omega/T, |\omega|<\pi$$

It can be shown that the corresponding impulse response of this discrete frequency response can be represented as:

$$h[n]=\{n\pi \cos [n\pi]+\sin [n\pi]\}/n^2\pi T - \infty<n<\infty$$

which is zero for n=0 and as follows for n not equal to zero:

$$h[n]=\{ \cos [n\pi]\}/nT.$$

An example of 6-point differentiator would be:

$$y[n]=\{x[n+3]/3-x[n+2]/2+x[n+1]-x[n-1]+x[n-2]/2-x[n-3]/3\}/T$$

A preferred moving average (MA) differentiator 91 with a linear slope bandwidth=±35 Hz and the following transfer function and recursive formula:

$$H(z)=-z^{-3}-2z^{-2}+2z^2+z^4$$

$$y[n]=-x[n-3]-2x[n-2]+2x[n+2]+x[n+3]$$

where K=3, T=500 Hz and Delay=3T.

The differentiated array is then further nonlinear scaled in 92, preferably squared to enhance the spikes:

$$y[n]=y[n]*y[n]$$

The non-linear squared signal is then further searched in 93 for a maximum value Max, then Max/2 is used as the dynamical threshold to detect any spikes within the array that are larger than the threshold. The 1st 2 consecutive spikes are used to determine the airway pressure signal period $T_P$. Then $T_P$ is stored onto memory board 70, block #4, for global variable use.

On board #3 in 100, the A/D converter #2 works in a sample-analysis-sample mode. The sample duration is a preset short time period $T_S$ at the level of mini seconds, for example, $T_S$=50 mini seconds. At the sample rate of 500 Hz, 50 mini seconds represents 25 data points which allow any simple data analysis, such as low-pass filtering 101, data searching 102 and data comparing 103 of the 25 data points, be done by a microprocessor like 41, 51 and 61 also within the level of mini seconds. This extremely fast mode of on-off-on allows us to achieve a near real-time operation that guarantees a quick response time to activate/inactivate the bovie according the always changing maximum airway pressure, as a result, avoiding an iatrogenic injury to the lungs or other living tissue.

The sampled $T_S$ duration of signal in 100 is then low-pass filtered by an all-integer-coefficient digital filter 101 to eliminate 60 Hz or higher frequency interference. A preferred low-pass auto-regressive moving average filter 101 for this invention is employed having a nominal bandwidth=±55.5 Hz, sidelobes=−27 dB, k=9, T=0.002 Sec (for sample rate of 500 Hz), Delay=1T, Gain=81, having the following transfer function and recursive formula:

$$H(z)=(1-z^{-9})^2/(1-z^{-1})^2$$

$$y[n]=2y[n-1]-y[n-2]+x[n]-2x[n-9]+x[n-18]$$

The low-pass filtered signal is then stored into the memory board 70, block #2, for further processing.

The low-pass filtered signal is then further searched in 102 for maximum and minimum values $S_{max}$ and $S_{min}$. Then $S_{max}$ is compared with $P_{threshold}$ in 103, namely, $$S_{max} > P_{threshold}?$$

If the answer is "YES", then a relay control signal is set to "0" which inactivates the bovie. If the answer is "NO", then a relay control signal is set to "1" which activates the bovie. After the control signal is sent, board #3 repeats the on-off-on process iteratively again from 100.

We claim:

1. A method of providing a lung protection function in an electrocautery system, the said method comprising the steps of:
   converting a patient airway pressure signal in a ventilator or an anesthesia machine into an electrical signal with a pressure transducer placed inside the patient endotracheal tubing system or in an inspiratory limb or expiratory limb internal to the ventilator or the anesthesia machine; and
   generating an auto-correlation function of data from the converted electrical airway pressure signal for a selected portion spanning at least one and half of a respiration period/cycle iteratively and dynamically; and
   determining maximum and minimum values of the electrical airway pressure signal from an iteratively and dynamically updated duration that is a function of the determined airway pressure signal period/cycle; and
   calculating a threshold from the determined maximum and minimum values and comparing the threshold with actual live patient electrical airway pressure signal, activating/inactivating a bovie accordingly in real-time.

2. The method of claim 1 wherein the determining step comprises the steps of:
   determining a maximum amplitude value of the auto-correlation function; and
   determining a series of time occurrences in a selected portion of the auto-correlation function at least as great as a predetermined fractional value of the maximum amplitude value.

3. The method of claim 2 wherein the amplitude value identifying step comprises the steps of:
   initially identifying a time of occurrence of a maximum amplitude value in the selected portion of the auto-correlation function; and
   identifying a first amplitude value of the auto-correlation function at least as great as a predetermined fractional value of the maximum amplitude value occurring in the auto-correlation function; and
   identifying a second amplitude value of the auto-correlation function at least as great as the predetermined fractional value of the maximum amplitude value occurring in the auto-correlation function.

4. The method of claim 3 further comprising the steps of determining a respiration period/cycle of the patient electrical airway pressure signal from a difference between time of occurrence of a first determined maximum amplitude value of the auto-correlation function and the time of occurrence of a second determined maximum amplitude value of the auto-correlation function.

5. The method of claim 1 wherein the step of generating the auto-correlation function comprises generating a Fast Fourier Transform derived auto-correlation function of a selected portion of the electrical airway pressure signal.

6. The method of claim 5 wherein the step of generating the auto-correlation function further comprises generating the auto-correlation function with a zero padding function.

7. The method of claim 1 further comprising the initial steps of:
   differentiating the auto-correlation function with respect to time; and
   scaling the differentiated auto-correlation function non-linearly to emphasize amplitude peaks in the differentiated auto-correlation; and
   identifying a maximum amplitude value of the scaled function occurring in an interval including at least one and half of a respiration period/cycle of the auto-correlation function; and
   identifying each amplitude value of the scaled auto-correlation in the selected interval at least as great as a predetermined fraction of the maximum amplitude value.

8. The method of claim 7 wherein identifying each amplitude value at least as great as one half of the maximum amplitude value.

9. The method of claim 1 further comprising the step of initially filtering the electrical airway pressure signal to remove high frequency components from sources of electrical interference external to the patient and wherein the generating step comprises generating the auto-correlation function from the filtered electrical airway pressure signal.

10. The method of claim 9 wherein the filtering step comprises removing frequency components of about 55 Hz or more from the electrical airway pressure signal.

11. The method of claim 9 wherein the electrical airway pressure signal data is digitized and the filtering step comprises passing the digitized electrical signal through an all-integer-coefficient filter.

12. The method of claim 1 wherein the searching the maximal and minimal values of the electrical airway pressure signal comprises steps of:

determining the maximal and minimal values of said electrical airway pressure signal; and computing a value as A which equals to 90% of a range between said minimal to said maximal value; and computing a value as B which equals to 75% of the range between said minimal value and maximal value; and if user selects up 10% (of lung expansion) lung protection, inactivating bovie when the value of said electrical airway pressure signal is at/or above said value A; if user selects up 25% (of lung expansion) lung protection, inactivating bovie when the value of said electrical airway pressure signal is at or above said value B.

13. The method of claim 12 wherein the selection of the value A, B can be other any percentage less than 70%.

14. The method of claim 12 wherein the selection can be more than two (10% and 25%).

15. The method of claim 1 wherein using the threshold to compare with the actual live patient electrical airway pressure signal, therefore, activating/inactivating the bovie accordingly in real-time comprises steps of:

a very short time duration of the electrical airway pressure signal is digitized; and initially filtering the said electrical airway pressure signal to remove high frequency components from sources of electrical interference external to the patient; and determining the maximal and minimal values of the said filtered electrical airway pressure signal; and comparing the maximal and minimal values with the determined threshold to activate/inactivate a relay device 11 that controls the bovie unit; and continuing above said method steps iteratively for as long as main power is on.

16. The method of claim 15 wherein digitizing a short time duration comprises digitizing the electrical airway pressure signal for a short duration of 50 mini seconds.

17. The method of claim 15 wherein the filtering step comprises removing frequency components of about 55 Hz or more from the electrical airway pressure signal.

18. The method of claim 15 wherein the electrical airway pressure signal data is digitized and the filtering step comprises passing the digitized electrical signal through an all-integer-coefficient filter.

19. Apparatus for providing a lung protection function in an electrocautery, the said apparatus comprising:

means to obtain a airway pressure in patient endotracheal tubing system or in an inspiratory limb or expiratory limb internal to a ventilator or an anesthesia machine; and means to digitize the electrical airway pressure signal into digital data;

means to perform computation, such as a programmable computer or a microprocessor; and means to perform large scale digital signal processing, such as a digital signal processing chip.

20. Apparatus for providing a lung protection function in an electrocautery, the said apparatus comprising:

external buttons to select continuous or discrete protection control levels; and an external button to perform function of up 10% lung protection; an external button to perform function of up 25% lung protection; an external button to shut down lung protection function only; and computer means connected to receive data from an electrical airway pressure signal determining means.

* * * * *